United States Patent [19]
Watson et al.

[11] Patent Number: 5,409,466
[45] Date of Patent: Apr. 25, 1995

[54] TRANSDERMAL INJECTION APPLIANCE

[76] Inventors: Robert L. Watson, 1600 Singletree Way, Bowling Green, Ky. 42103; Robert C. Shober, Jr., P.O. Box 143, Alvaton, Ky. 42122

[21] Appl. No.: 186,280

[22] Filed: Jan. 25, 1994

Related U.S. Application Data

[62] Division of Ser. No. 109,935, Aug. 17, 1993, Pat. No. 5,342,319.

[51] Int. Cl.⁶ ............................................. A61M 5/32
[52] U.S. Cl. .................................... 604/198; 604/180
[58] Field of Search ............... 604/192, 193, 198, 53, 604/51, 180

[56] References Cited

U.S. PATENT DOCUMENTS 4,564,054 12/1986 Gustavsson .................... 604/198
5,269,765 12/1993 Kuracina ....................... 604/198

Primary Examiner—John G. Weiss
Attorney, Agent, or Firm—Walter C. Farley

[57] ABSTRACT

A transdermal injection appliance has a pad impregnated with a disinfectant solution such as alcohol, a body with adhesive for holding the pad against the skin of a patient, and a sleeve with a guide passage through the body for guiding an injection needle. A membrane puncturable by the needle is attached to the sleeve to close the passage, the membrane being self-sealing so that an opening through the membrane formed by the needle is closed as soon as the needle is extracted, thereby wiping a majority of blood from the needle and preventing the escape of blood. The tubular sleeve can have an outer end with a coupling for connection to a retractable needle injection assembly. A method of using the appliance with the retractable needle assembly to administer medication without exposing the health care giver to accidental contact with the needle is also disclosed.

1 Claim, 5 Drawing Sheets

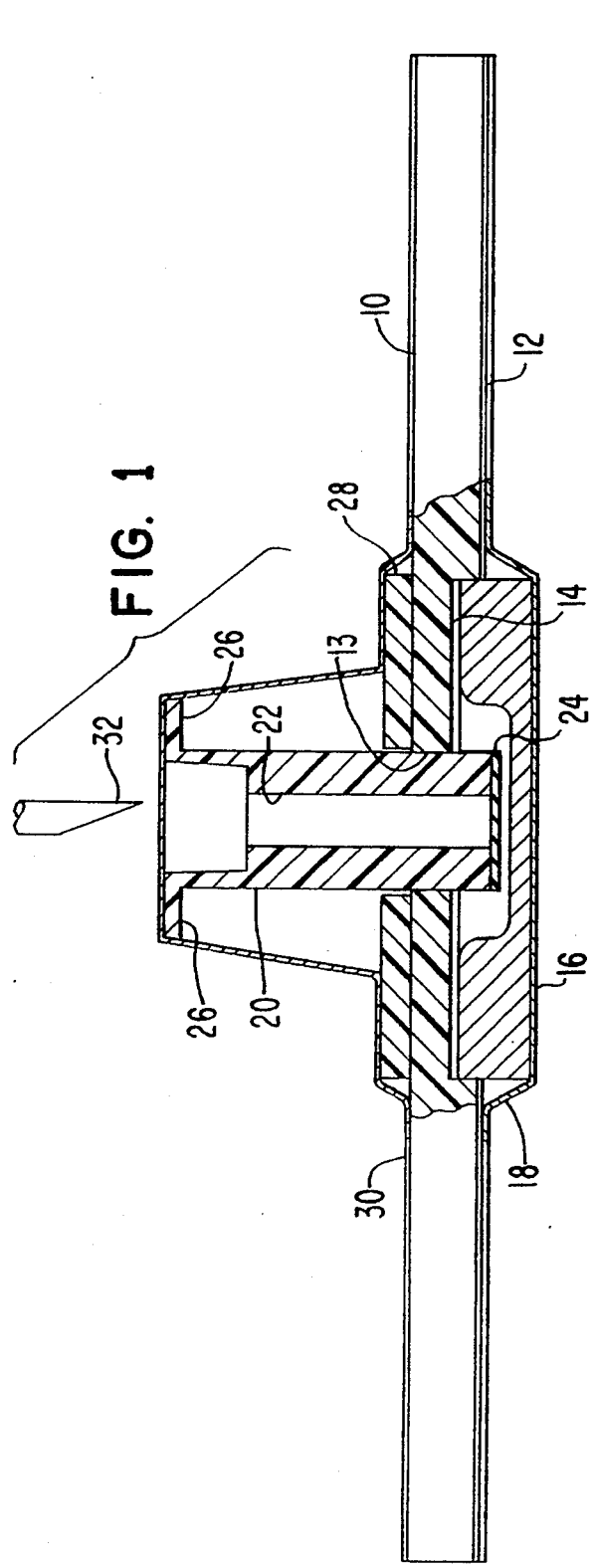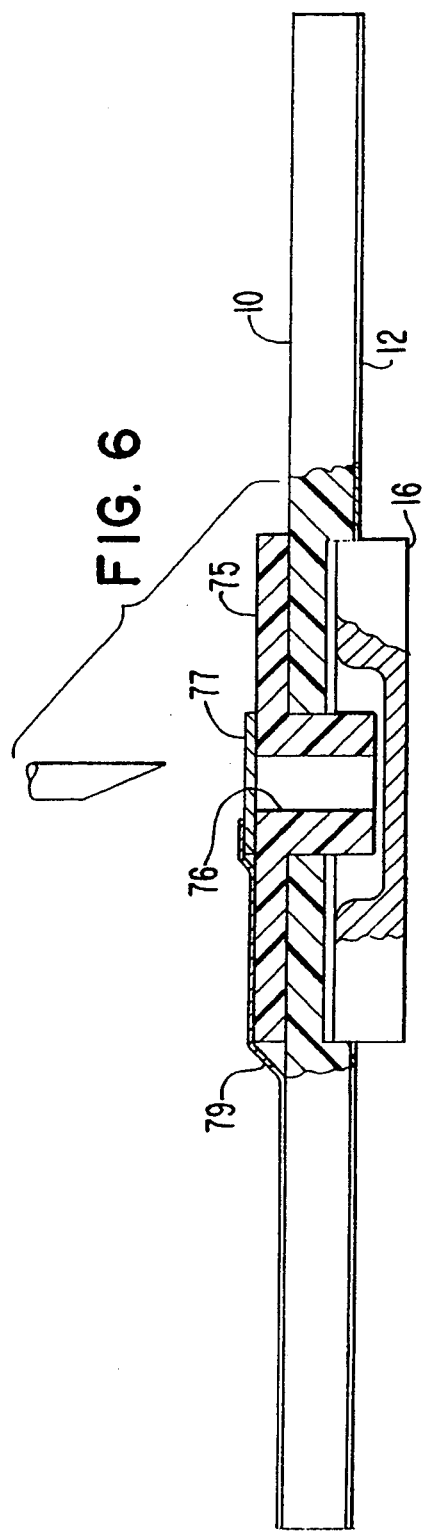

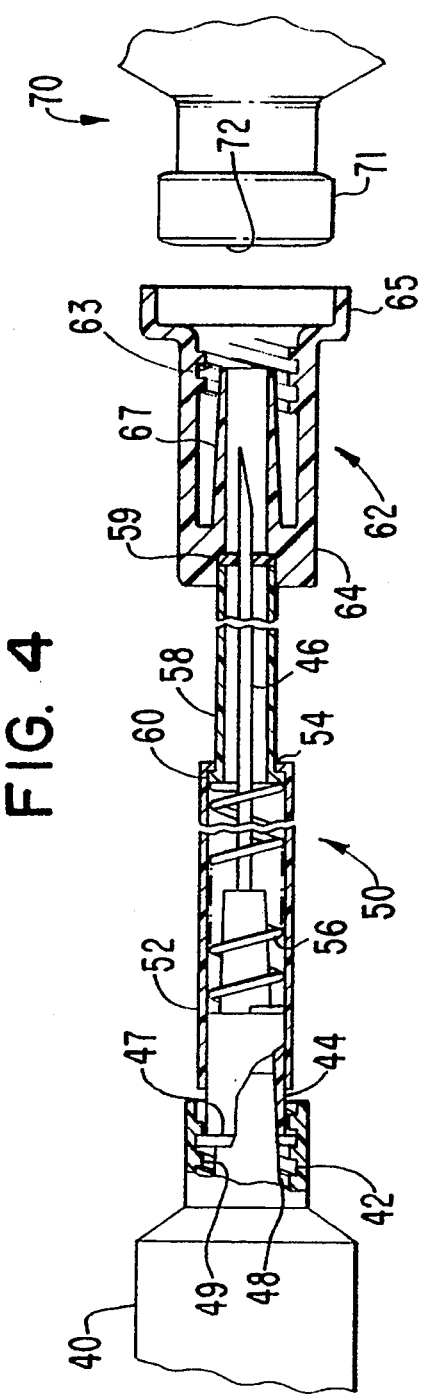
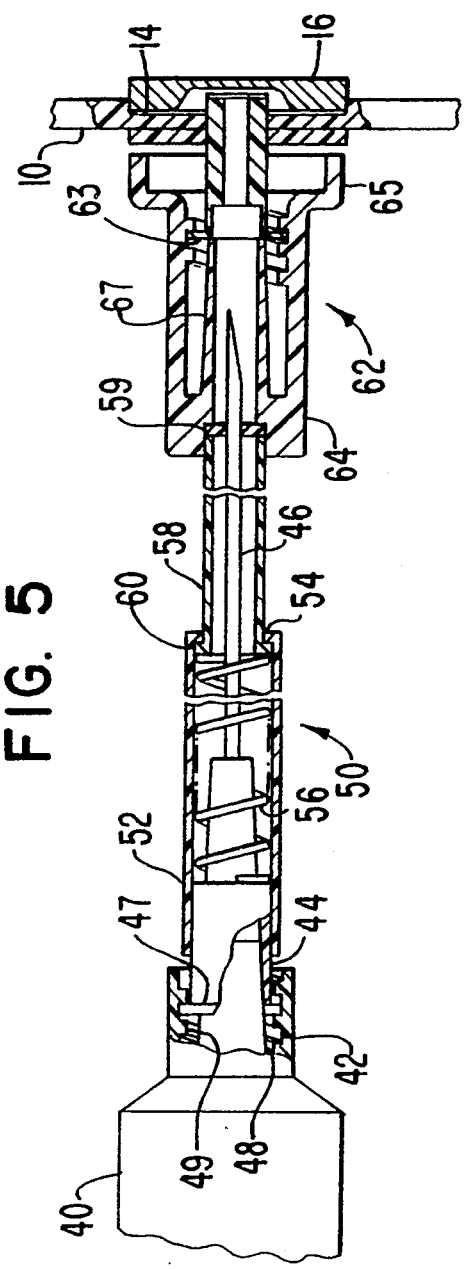

5,409,466

TRANSDERMAL INJECTION APPLIANCE

CROSS-REFERENCE TO RELATED APPLICATION

This is a division of application Ser. No. 08/109,935 filed Aug. 17, 1993, now U.S. Pat. No. 5,342,319.

FIELD OF THE INVENTION

This invention relates to an appliance for facilitating the safe use of an injection needle by protecting the health care provider from accidental contact with the needle and also protecting the provider from contact with the blood of a patient.

CROSS-REFERENCE TO RELATED APPLICATION

The device of this invention is advantageously used in conjunction with a retractable injection needle assembly disclosed and claimed in U.S. patent application Ser. No. 936,338, Shober et al, filed Aug. 28, 1992, now U.S. Pat. No. 5,279,583, which is hereby incorporated by reference.

BACKGROUND OF THE INVENTION

U.S. patent application Ser. No. 936,338 discloses a needle assembly which has the advantages of housing a needle so that the user is protected from accidental puncture. In that apparatus, a syringe is coupled to a housing which contains the needle and covers it unless intentional steps are taken to cause the point to be exposed during connection to a medication container, a medication delivery apparatus or during intravenous or transcutaneous injection.

However, that application does not treat the problems associated with contact of the health care provider with the blood or serum of the patient during or after an injection. Since contact with the blood or serum of a person infected with certain contagious viruses can be highly dangerous, it is important to avoid such contact.

Normally, before an injection, the area of the skin to be punctured is cleaned with a substance such as alcohol. Following the injection, the needle puncture bleeds to some extent and is typically covered with sterile cotton, sometimes held in place with someone's finger or a small adhesive bandage. A danger exists that accidental contact with the blood emanating from the puncture can occur at that stage of the process.

SUMMARY OF THE INVENTION

Accordingly, an object of the present invention is to provide an appliance that permits transdermal administration of medication by injection with a hypodermic needle and eliminates exposure of the health care provider to blood or an exposed needle and which is also useful as a penetration site for an intravenous (IV) catheter.

A further object is to provide such an appliance which includes means for decontaminating the skin and a self-sealing membrane through which an injection needle can be inserted and withdrawn.

Another object is to provide an appliance which is suited for attachment to the skin of a patient to facilitate injection and which can be left on the patient following injection until after the injection puncture has stopped bleeding.

A still further object is to provide such an appliance which is provided with a coupling for connection of a retractable needle injection assembly.

Briefly described, the invention comprises a disk having adhesive means for holding the disk on the skin of a patient. The disk has a pad with alcohol or a similar disinfectant therein. A central guide passage through the disk allows the passage of an injection needle, the passage being closed by a membrane which can be punctured by the needle and which is self-sealing so that an opening through the membrane formed by the needle is closed as soon as the needle is extracted, thereby preventing the escape of blood.

The disk itself may alternatively or additionally be impregnated with the disinfectant, allowing the separate pad to be omitted. The membrane can also be a laminated body. When the needle is withdrawn, the needle is wiped relatively clean by a layer of the membrane, reducing exposure to blood.

Additionally, the disk preferably has a coupling for connection to a retractable needle injection assembly.

BRIEF DESCRIPTION OF THE DRAWINGS

In order to impart full understanding of the manner in which these and other objects are attained in accordance with the invention, particularly advantageous embodiments thereof will be described with reference to the accompanying drawings, which form a part of this disclosure, and wherein:

FIG. 1 is an enlarged side elevation, in partial section, of a first embodiment of an appliance in accordance with the invention;

FIG. 4 is a side elevation, in section, of an automatic needle retracting syringe assembly usable to extract medication from a supply vial;

FIG. 5 is a side elevation, in section of the automatic needle retracting syringe assembly of FIG. 4 coupled to an appliance in accordance with the present invention;

FIG. 6 is a side elevation in partial section of a further embodiment of the invention;

DESCRIPTION OF THE PREFERRED EMBODIMENTS

Figure 2:
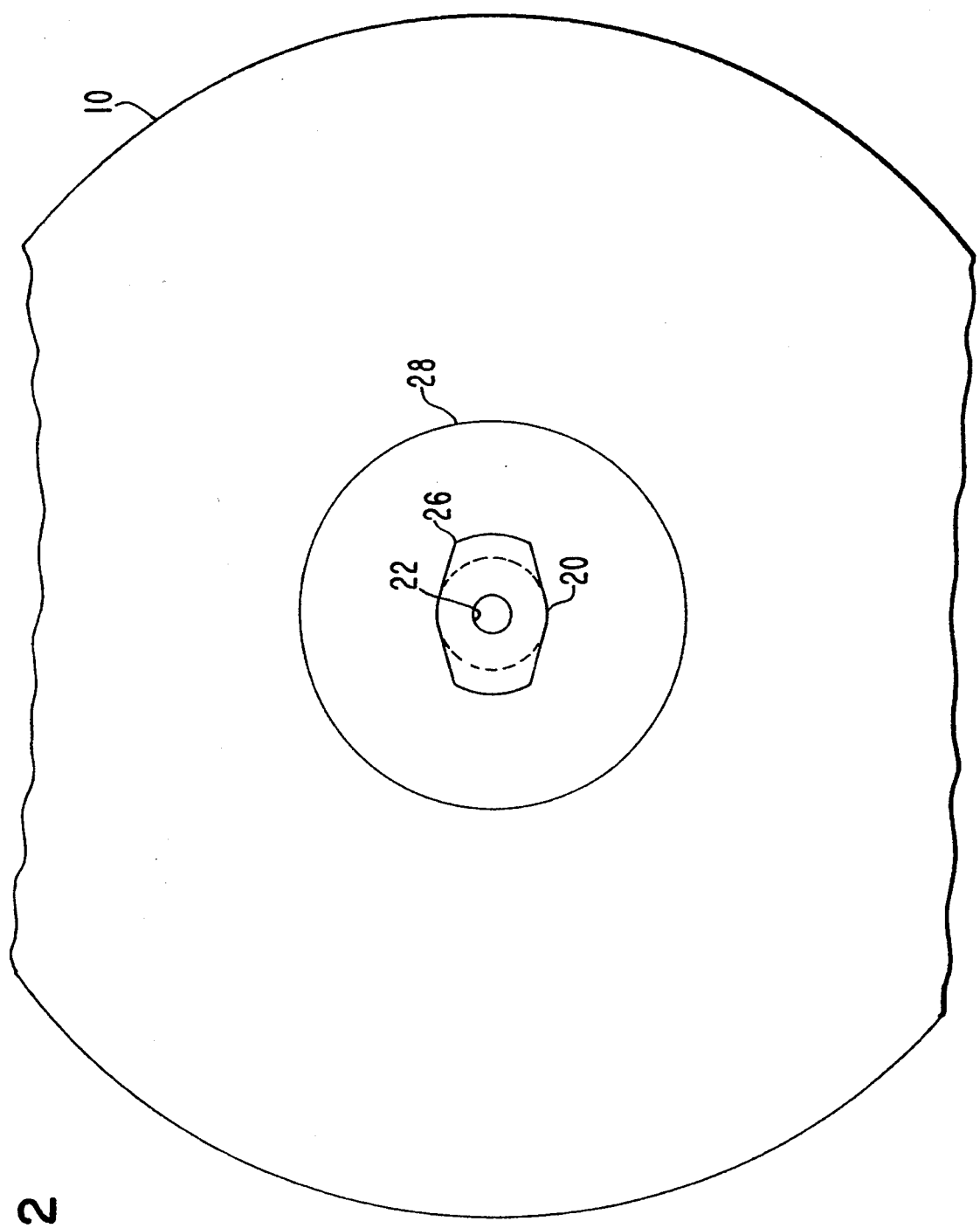
FIG. 2 is a partial top plan view of the device of FIG. 1 with a top cover removed.
Figure 3:
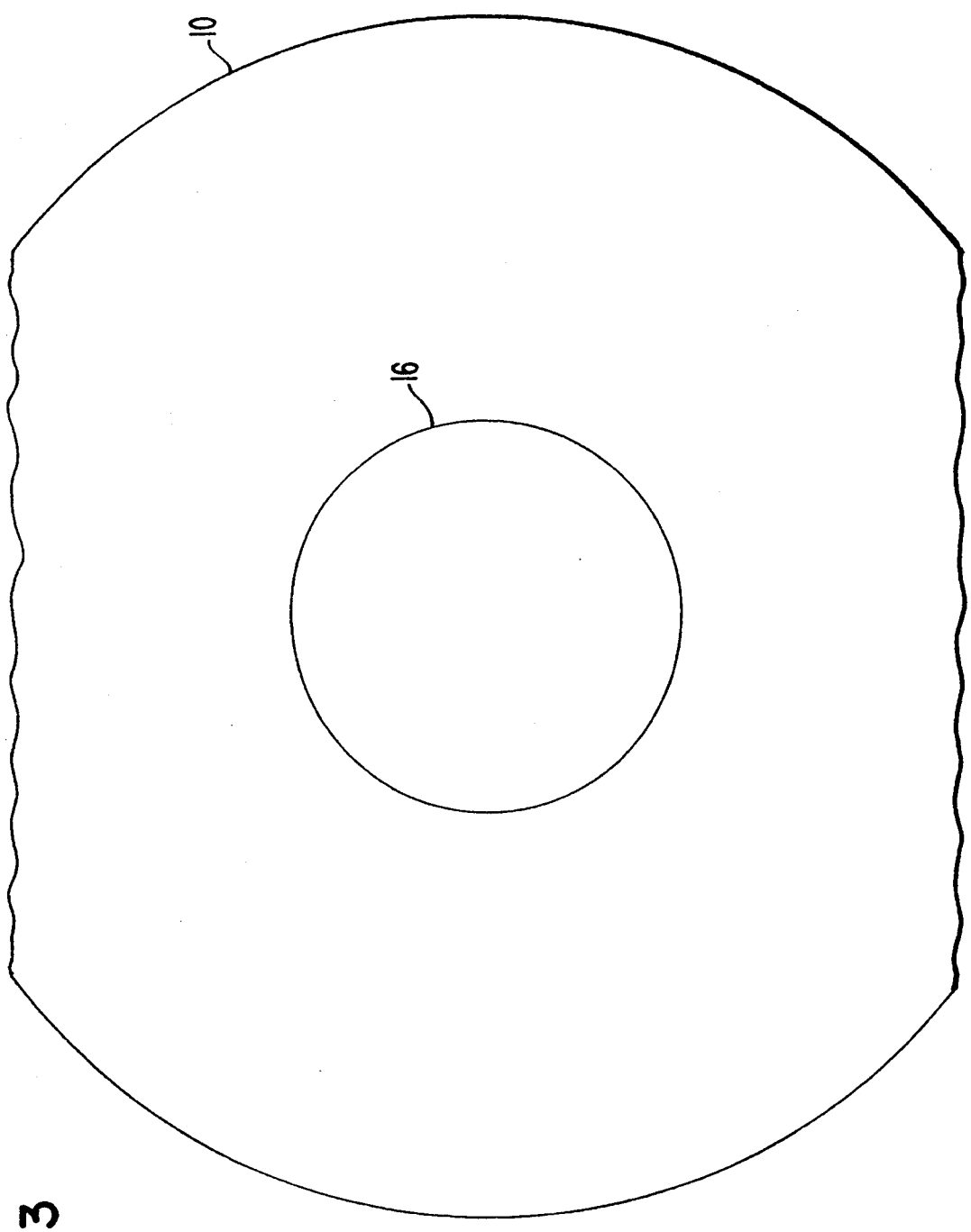
FIG. 3 is a partial bottom plan view of the device of FIGS. 1 and 2 with a bottom cover removed.

Referring to FIGS. 1-3, the appliance includes an annular, disk-shaped body 10 which is preferably made of a soft elastomer or flexible foam, of either the open- or closed-cell type. Body 10 has a coating 12 of an adhesive such as is commonly used on small adhesive bandages, the primary characteristics of the adhesive being that it is capable of adhering to human skin without harming the skin. Body 10 has a central opening 13 and a recess 14 which receives a disk-shaped, alcohol-impregnated pad 16. Pad 16 is made of a compressible material and is formed with a central recess so that it can be compressed largely into recess 14. Pad 16 can also, or alternatively, be impregnated with a topical anesthetic or disinfectant. A removable and disposable cover 18 is shaped to cover the adhesive surface 12 of body 10 as well as the exposed surface of pad 16. Cover 18 is made of a material which releases from the adhesive in the manner of the disposable covers for a conventional adhesive bandage.

A tubular plastic sleeve 20 extends into central opening 13 of the body, sleeve 20 having a central lumen 22 which is dimensioned to receive an injection needle. At the inner or lower end of sleeve 20 is a resealable laminated membrane 24 made of a self-repairing elastomeric material such as Silastic or latex. In addition to being self-sealing so that it closes after a needle has passed therethrough and been removed, membrane 24 is impervious to blood and serum and should be compatible with skin contact.

At the outer or upper end of sleeve 20 are protruding ears 26 formed and dimensioned to act as one-half of a coupling such as a standard Luer-Lok ® fitting so that a retracting needle assembly in accordance with previously mentioned application Ser. No. 936,338 can be connected thereto. An annular, disk-shaped collar 28 of rather stiff or rigid plastic material can also be provided surrounding sleeve 20 for stabilizing purposes. Depending on the materials selected for the other components, collar 28 may not be necessary. However, if needed, it can conveniently be manufactured as an integral part of sleeve 20.

Finally, a peel-off dome cover 30 covers the upper surfaces of body 10, collar 28 and sleeve 20 until the device is ready for use.

In use, cover 18 is removed and discarded and the adhesive surface 12 of body 10 is pressed against the skin of a patient so that it adheres to the area surrounding the desired location for an injection. At this time, pad 16 is compressed by pressure with the skin and discharges a sufficient amount of alcohol to decontaminate the injection area. It is also possible for the health care provider to rub the area with the pad 16 before adhering body 10 to the skin. Alternatively or additionally, as mentioned above, the pad can contain an anesthetic to numb the injection area.

Cover 30 is then removed and an injection needle 32 is passed through lumen 22 of sleeve 20 and through membrane 24, puncturing the membrane. Lumen 22 guides the needle as it passes through pad 16 and into the skin of the patient to which body 10 is adhered. A syringe, not shown in FIGS. 1-3, is then actuated to discharge medication through needle 32 and into the patient in a conventional fashion.

The needle is then extracted from the patient and withdrawn through pad 16 and membrane 24. At this time, the membrane reseals itself, closing the opening so that any discharge of blood or serum from the injection puncture is prevented from entering lumen 22. The needle is disposed of in a standard manner. Body 10 is not removed from the patient's skin at this time. Rather, it remains so that the alcohol in the pad can continue to have a disinfecting effect and so that the pad can absorb the small amount of blood or serum discharge which commonly follows an injection. Because pad 16 is compressed when it is applied, it applies gentle pressure to the area of the puncture to stop bleeding. No separate cotton ball or bandage is required since the pad performs the functions thereof. After an hour or so, the entire device can be removed and discarded, the skin puncture having healed itself sufficiently to require no further attention in most cases.

As will be apparent to one skilled in the art, the appliance described thus far can be used with any conventional needle and syringe and is quite useful, but its use with a conventional, exposed needle does not solve the related problem of protecting the health care provider from possible contact with the needle before or after the injection is given. Contact with the needle after injection is, of course, at least as hazardous as contact with the blood or serum if the patient has a dangerous virus.

For this reason, provision is made for connection of sleeve 20 to the retractable needle assembly mentioned above. Before discussing that connection, reference is made to FIG. 4 which shows an automatic retracting needle assembly of application Ser. No. 936,338, mentioned above. This figure and a brief description thereof is included herein for convenience and to illustrate the use of these devices in conjunction with each other to form a medication administration system.

The apparatus will be described with reference to FIG. 4 in conjunction with a conventional syringe 40 of a type having an internally threaded collar 42 at the end thereof of a type sold under the trademark Luer-Lok ®. This kind of threaded collar is designed to receive the proximal end of a plastic fitting 44 holding an injection needle 46. Needles of various sizes are normally provided with a fitting similar to fitting 44 fixedly attached to the proximal end of the needle to facilitate connection of the needle to various devices such as syringes and the like, fitting 44 being similar to the fitting formed by flanges 26 of sleeve 20. The proximal end of fitting 44 has flanges 47 protruding radially in opposite directions, the peripheries of the flanges being dimensioned to be received between the lands of threads 49 within collar 42. A central spout or nipple 48 extends axially from the syringe within the threaded collar and frictionally engages a tapered interior surface of fitting 44, producing a tight fit which, in conjunction with the threads, holds the needle fitting in place and also provides a fluid-tight seal so that fluids from within the syringe 40 can be forced through the lumen of the needle. Fitting 44 also has a conical outer surface for frictionally engaging a cover or the like. Generally, the portion of the Luer-Lok ® fitting having the collar and central nipple is regarded as the male portion while that with the tapered interior surface and the flanges, like fitting 44, is regarded as the female portion.

Typically, the needle initially arrives from the manufacturer in a rigid safety sleeve, not shown, which encases the needle and frictionally engages the conical outside of fitting 44, the needle and sleeve being contained in a sterile package. When it is time to use the needle, the outer package is removed and flanges 47 are inserted into collar 42 and rotated to engage threads 49 and lock the needle fitting onto the syringe. The safety sleeve is then pulled off, exposing the needle for use. The needle is a conventional needle in the sense that it is hollow and has a slanted end terminating in a very sharp point to facilitate penetration of skin or a rubber or plastic membrane, as necessary.

An assembly 50 includes a tubular spring sleeve 52 which is substantially cylindrical, the inner diameter of the proximal end of sleeve 52 being selected to frictionally engage the outer conical surface of fitting 44. The distal end of sleeve 52 is formed with an inwardly extending flange 54. Within sleeve 52 is a compression coil spring 56.

The proximal end of a generally tubular needle-encasing sleeve 58 is received within sleeve 52 and is axially slidable therein, the proximal end of sleeve 58 having an outwardly extending flange 60 which engages flange 54 to prevent sleeve 58 from completely emerging from sleeve 52. As will be recognized, one end of spring 56 engages fitting 44 and the other end thereof abuts flange 60, the length of the spring being selected so that it urges flanges 54 and 60 into abutment with each other. Thus, sleeve 58 is telescopically movable between a first position shown in FIG. 4 in which flanges 54 and 60 are in abutment and a second position in which those flanges are spaced apart and spring 56 is compressed. In the second position, sleeve 58 is almost entirely contained within sleeve 52.

Attached to the distal end of sleeve 58 is an end coupling or bell indicated generally at 62 having a first, internally threaded portion 64 and a larger un-threaded skirt portion 65. Bell 62 is provided with a recess to receive the distal end of sleeve 58 and also a rubber diaphragm 59 which extends transversely across the end of sleeve 58 and is penetrated by needle 46 to form a seal preventing the flow of fluid from the bell into the interior of sleeve 58. The distal end of sleeve 58 is fixedly attached to bell 62 by an adhesive or by heat fusion of the members together. Portion 64 is formed substantially like fitting 42 in the sense that it has the same internal diameter and similarly formed internal threads 63 for the purpose of connection to a fitting like fitting 44, if desired, which may be attached to a needle or to some other fluid-conducting device. In addition, a spout 67 extends axially into the interior of threaded portion 64 to engage the interior of a needle fitting in the same manner as spout 48 engages the inner surface of fitting 44.

Enlargement 65 may be formed at the end of the bell and dimensioned to fit over the top of a conventional medication vial indicated generally at 70. A vial of this type generally has a metal top 71 which holds a resealable rubber diaphragm 72 across the end of the vial. To remove medication for delivery to a patient, a needle is pushed through the diaphragm and a syringe attached to the needle is pulled to extract the medication from the vial. To avoid the possibility of injury to the person performing this task, enlargement 65 is positioned on the bottle top, properly centering the needle for insertion through the diaphragm. This substantially eliminates the possibility that the needle might slip to one side and stick the user.

As soon as the needle is withdrawn from the vial, it is again housed within the protective sleeves, preventing accidental puncture of the health care provider. At this stage, the syringe is filled with medication and the apparatus is ready for injecting the medication into the patient.

Without causing the needle to protrude, coupling 62 is attached to the Luer-Lok ears 26 at the top of sleeve 20 by inserting the ears into threads 63 and rotating the syringe to lock the devices together. The assembly as shown in FIGS. 1-3 will have been applied to the patient's skin, as described above. The needle is then pushed into the patient's skin and the syringe is operated in a conventional manner to inject the medication. After injection, the needle is withdrawn from the patient and is automatically again housed within the protective sleeves. Once again, the user is protected from accidental puncture because the needle is totally protected.

At this stage, it will be recognized that the entire process of loading the syringe and injecting the medication has been accomplished without at any time exposing the user to the danger of accidental puncture and without exposing the user to accidental contact with the patient's blood or serum.

A further embodiment of a transdermal injection disk in accordance with the invention is shown in FIG. 6. In this embodiment, the body 10, pad 16 and adhesive coating are substantially the same as in the embodiment of FIGS. 1-3, including the cover 18 of FIG. 1 which has been omitted from FIG. 6. The central sleeve, however, is formed as a unitarily formed sleeve and disk unit 75 wherein the sleeve portion is shorter than in the embodiment of FIG. 1 and the outer end of the sleeve portion is substantially flush with the outer surface of the disk portion. Sleeve 75 has a central lumen 76 dimensioned to receive and guide an injection needle. A resealable membrane 77 is attached to the outer end of sleeve 75 and is therefore punctured by the injection needle before the needle enters lumen 76. An outer cover 79 covers the membrane and the outer surfaces of disk 28 and body 10 and is removed before use. Membrane 77 can also be applied to the outer end of the sleeve in the embodiment of FIGS. 1-3 so long as it is attached in such a way that it does not interfere with attachment to the retractable injection needle assembly.

Figure 7:
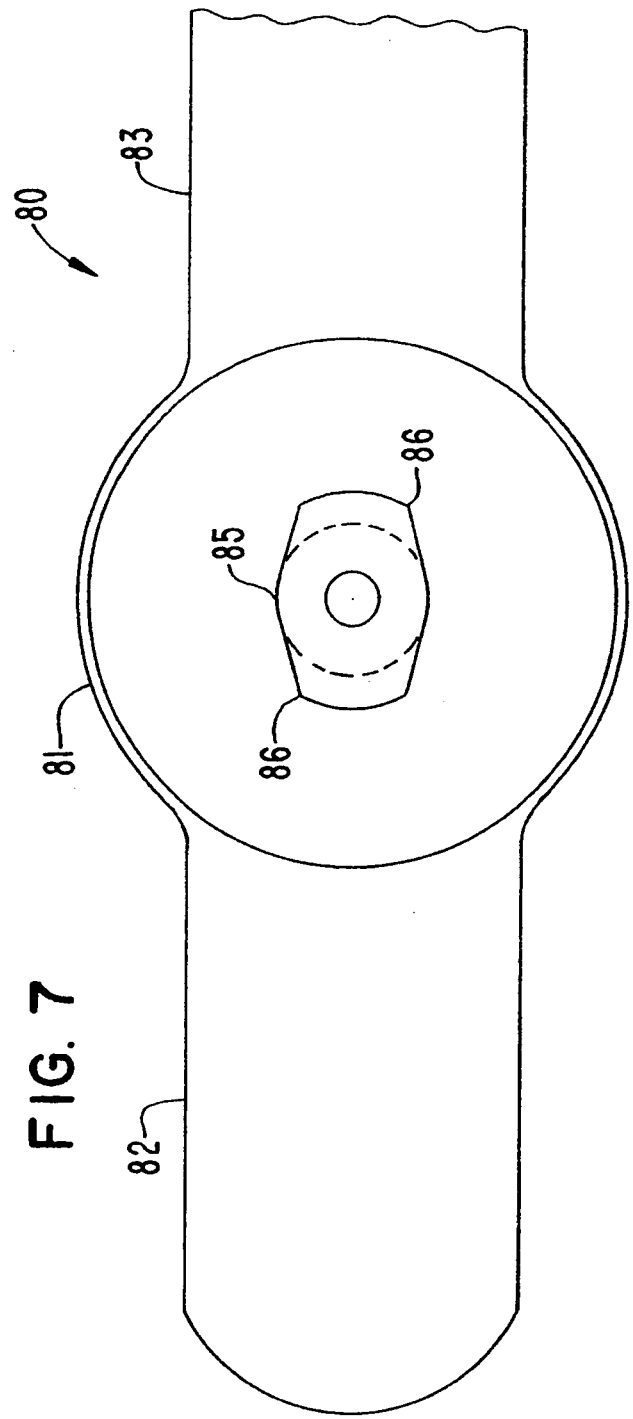
FIG. 7 is a top plan view of another embodiment of the present invention.

FIG. 7 is a top plan view of a still further embodiment of an appliance in accordance with the invention wherein a body indicated generally at 80 has a central circular portion 81 which is similar in size to a central reinforcing disk 84. Attachment tabs 82 and 83 extend radially outwardly from body portion 81, all portions thereof being coated with adhesive for attachment to the skin. A pad is received in a recess on the bottom side of the central body portion essentially as shown in FIG. 1. A sleeve 85 with coupling flanges 86 is attached as in the embodiment of FIGS. 1-3 or a sleeve is attached as shown in FIG. 6. Functionally, the embodiment of FIG. 7 is similar to those described heretofore. The advantage of the FIG. 7 embodiment is that it is smaller in overall size and may be usable in areas where use of the overall circular body may be inconvenient, although it has less absorbing area.

Figure 8:
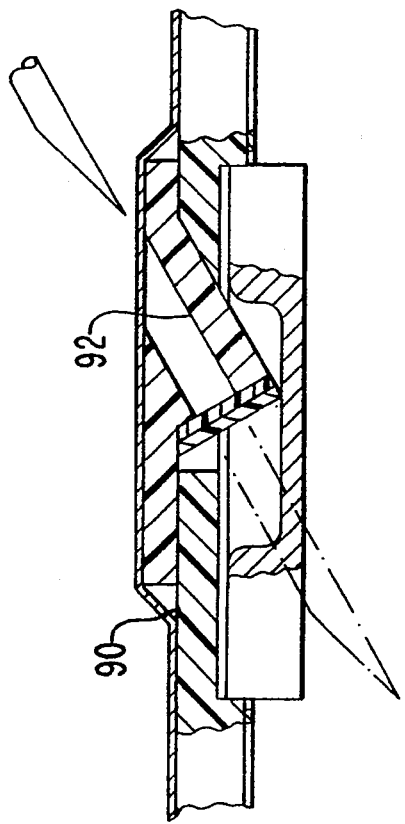
FIG. 8 is a side view, in section, of yet another embodiment of the invention.

FIG. 8 shows an embodiment which is intended primarily to facilitate IV injections. In this embodiment, a body 10 is formed with a tubular guide 92 the central axis of which lies at an acute angle relative to the plane containing the major surfaces of the body. Preferably, the angle is between about 15° and 30°. As in the other embodiments, passage 92 is dimensioned to receive a needle 32 which is guided into a blood vessel for injecting medication, saline solution or other substances. An arrangement to perform this function also can be constructed in a manner similar to FIG. 1 or FIG. 6 but with a bellows arrangement interconnecting sleeve 20 (or the equivalent guide sleeve in FIG. 6) to body 10 so that the angle of the guide tube is adjustable. While this is more flexible in its applications, it is also more complex and expensive in construction.

FIG. 8 also illustrates the use of a laminated membrane having a layer 94 of an elastomeric material and a layer 95 of a material such as foam or the like impregnated with a disinfectant. The other characteristics of this embodiment are similar to the other embodiments described and will not be repeated.

While certain advantageous embodiments have been chosen to illustrate the invention, it will be understood by those skilled in the art that various changes and modifications can be made therein without departing from the scope of the invention as defined in the appended claims.

What is claimed is:

1. A method of administering medication to a patient using an injection needle without exposing the needle comprising the steps of providing a retractable needle assembly including an injection needle, a housing having a first portion attached to the needle, a second portion movable relative to the first portion between an extended position in which the needle is enclosed and a retracted position in which part of said needle is exposed, coupling the assembly to a medication container, moving the second portion to the retracted position and extracting medication from the container, moving the second portion to the extended position enclosing the needle, detaching the needle assembly from the container, adhering directly to the skin of the patient an appliance having coupling means thereon matable with said second portion, coupling the needle assembly to the appliance, moving the second portion to the retracted position, and administering the medication to the patient by extending the needle so that the needle passes through the appliance and the patient's skin, and removing the needle assembly from said appliance, leaving the appliance adhered to the patient's skin.

* * * * *